United States Patent
Dame et al.

(10) Patent No.: US 7,166,118 B2
(45) Date of Patent: Jan. 23, 2007

(54) MICROKERATOME BLADE ASSEMBLY

(75) Inventors: Randy Dame, Manchester, MO (US); Michael L. Smith, Union, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 512 days.

(21) Appl. No.: 10/307,017

(22) Filed: Nov. 27, 2002

(65) Prior Publication Data

US 2004/0102798 A1    May 27, 2004

(51) Int. Cl.
*A61F 9/007*    (2006.01)
*A61B 17/32*    (2006.01)

(52) U.S. Cl. ......................... 606/166; 30/329

(58) Field of Classification Search ............... 606/107, 606/166, 167; 30/37, 32, 34.05, 43.1, 493, 30/142, 526, 329
See application file for complete search history.

(56) References Cited

U.S. PATENT DOCUMENTS

| | | | |
|---|---|---|---|
| 4,959,065 A | * | 9/1990 | Arnett et al. ................. 606/69 |
| 6,051,009 A | * | 4/2000 | Hellenkamp et al. ....... 606/166 |
| 6,663,644 B1 | * | 12/2003 | Ross et al. ................... 606/166 |
| 2002/0045910 A1 | * | 4/2002 | Aufaure et al. ............. 606/166 |
| 2002/0052615 A1 | | 5/2002 | Ross et al. ................... 606/166 |

FOREIGN PATENT DOCUMENTS

| | | |
|---|---|---|
| FR | 2 823 664 A1 | 10/2002 |
| WO | WO 01/97729 A1 | 12/2001 |
| WO | WO 02/03884 A2 | 1/2002 |

* cited by examiner

*Primary Examiner*—Anhtuan T. Nguyen
*Assistant Examiner*—Elizabeth Houston

(57) ABSTRACT

Blade assembly 18 for use in a microkeratome during eye surgery includes a cutting blade 20 and a blade holder 22 attached to the blade 20. Tabs 30 are attached to the blade holder 22 to assist in aligning the blade assembly 18 with a mating slot 12 in a microkeratome to minimize damage to the cutting blade 20. Tab 30 is attached to the blade holder 22, such that the tab 30 may be detached from the blade holder 22 after insertion into the microkeratome.

2 Claims, 1 Drawing Sheet

MICROKERATOME BLADE ASSEMBLY

BACKGROUND OF THE INVENTION

1. Field of the Invention

The present invention is related to keratome blades for use in eye surgery and more specifically, to microkeratome blades having an attached blade holder.

2. Description of Related Art

Microkeratome blades are well known in the art, and are typically used to cut corneal tissue. Within the last several years, these blades have typically been used to make a corneal flap during Laser Assisted In-situ Keratomileusis (LASIK).

Typically, these microkeratome blades and blade assemblies are driven across the cornea either in a straight line or arcuate fashion either manually or via a motor. Also, typically the microkeratome blade oscillates in a plane perpendicular to the direction of travel of the blade to help in assisting the cutting of the corneal tissue. The sharpness of the blade is particularly important to ensure that a clean, precise cut of the corneal flap is achieved. It is common that corneal flaps thicknesses between 120 and 200 microns are typically formed. With such a thin layer of corneal tissue being created, it is important that the sharpness and integrity of the blade be maintained throughout the operation.

This includes avoiding damage while inserting the blade into a microkeratome head assembly. To assist the microkeratome user while inserting the blade assembly into a microkeratome cutting head several alternatives have been used. One such method is described in U.S. Pat. No. 6,051,009 to Hellenkamp, et al. and is hereby incorporated in its entirety by reference. Hellenkamp, et al. teaches the use of a handle assembly that is threaded into a microkeratome blade assembly. The handle can then be manipulated so that the microkeratome blade slides into the mating slot of the microkeratome cutting head assembly. Once the blade assembly is inserted into the cutting head, the handle assembly is unthreaded from the blade holder. Other methods to insert the blade assembly into the microkeratome cutting head assembly have been the use of forceps or simply a user's fingers.

Because of the tight tolerances needed to hold the blade assembly securely in the cutting head assembly and because the blade is at an obtuse angle relative to the blade holder, damage often occurs to the blade, especially the cutting edge of the blade that is first inserted into the cutting head assembly.

It would therefore be desirable to provide some sort of alignment or guide that would help prevent damage to the blade upon insertion into the cutting head assembly. It also would be convenient if such a blade assembly were to have a handle attached to the blade holder so that any extra handle assembly or instruments to insert the blade assembly into the cutting head assembly can be eliminated.

DETAILED DESCRIPTION OF THE DRAWINGS

Figure 1:
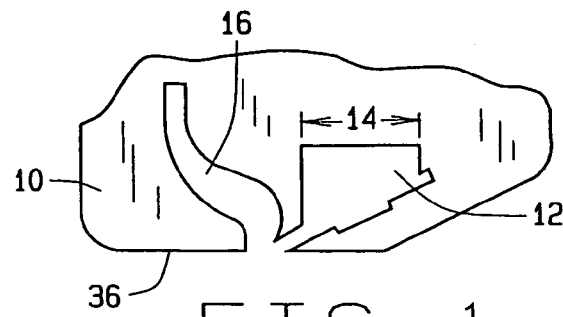
FIG. 1 is a partial view of a prior art cutting head assembly.

FIG. 1 shows a cut-away, partial view of a prior art microkeratome cutting head assembly 10 having a slot or structure 12 for accepting a cutting blade assembly. Slot 12 has a width 14 for accepting a blade holder of a cutting blade assembly. In addition, the cutting head assembly 10 has a slot 16 for receiving a corneal flap that is formed when using the microkeratome. The microkeratome cutting head assembly 10 is similar to that described in U.S. Pat. No. 6,051,009 to Hellenkamp, et al. which patent is herein incorporated in its entirety by reference.

Figure 2:
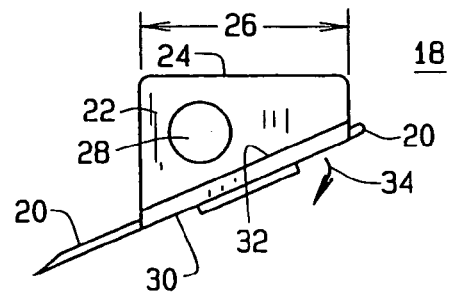
FIG. 2 is a side elevation of a blade assembly in accordance with the present invention.

FIG. 2 shows a side elevation view of a blade assembly 18 in accordance with the present invention. Blade assembly 18 includes a cutting blade 20 and a blade holder 22 attached to blade 20. Blade holder 22 has a top surface 24 and a width 26, which may be machined or molded to fit within the width 14 of FIG. 1. Blade holder 22 also includes a hole 28 for threadingly receiving a hand tool as described in Hellenkamp, et al. In addition, blade assembly 18 includes tabs 30 attached to the blade holder 22 so that at least one tab 30 is structured to assist in aligning the blade assembly 18 with the mating slot 12 in the microkeratome to minimize damage to the cutting blade 20. Tabs 30 are attached to the blade holder 22 via fingers 32, such that the tabs 30 may be detached from the blade holder 22 after insertion into the microkeratome. Tabs 30 are preferably removed by twisting the tabs in the direction of arrows 34 and finger 32 is sufficiently narrow to become easily disengaged from blade holder 22 upon twisting.

It is noted that blade assembly 18 may only have one tab instead of the two (2) tabs shown. In the case of only one tab 30, the insertion handle of the prior art is preferably used to insert the blade assembly 18 into the cutting head 10. In use, blade assembly 18 is inserted into the mating slot 12 and the tab 30 at the leading insertion side of the blade assembly 18 fits within the width 14 of FIG. 1 and is sufficiently thick to prevent rocking of the blade assembly once the tab 30 is within slot 12 such that tab 30 helps prevent damage to the cutting edge of cutting blade 20. Preventing damage to the cutting blade can be extremely helpful in the eye surgery as forming a corneal flap for LASIK surgery is a very precise procedure, and any damage to cutting blade 20 would significantly reduce the chances for a successful outcome.

Figure 3:
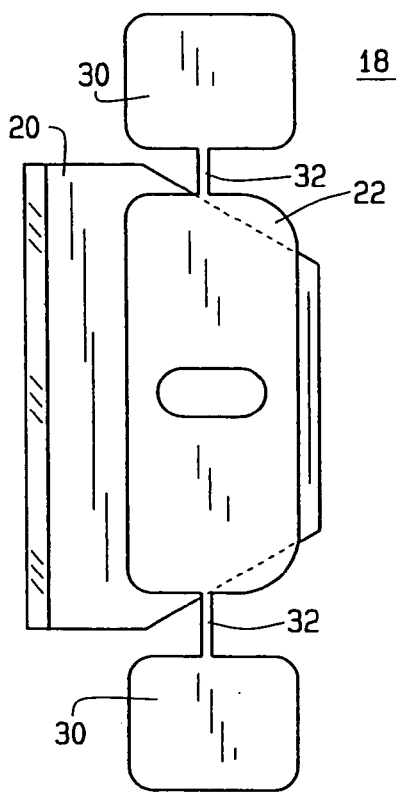
FIG. 3 is a top view of a blade assembly in accordance with the present invention.
Figure 4:
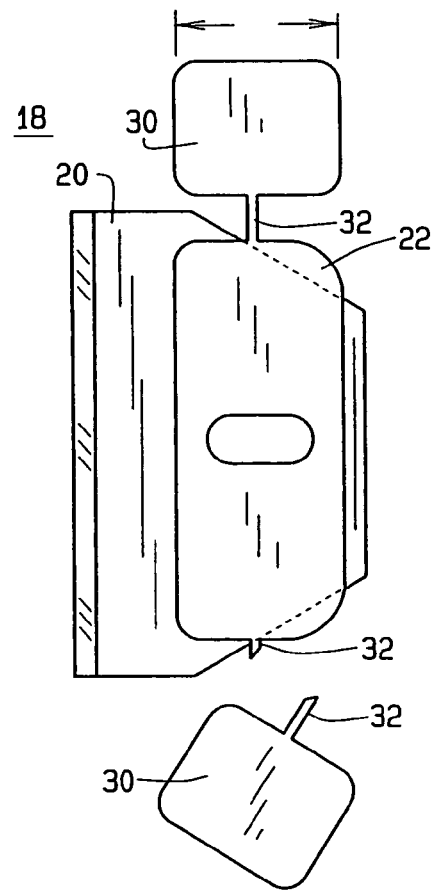
FIG. 4 is a top view of a blade assembly in accordance with the present invention, wherein one of the tabs has been removed.

As can be seen in FIG. 2, the tabs 30 are preferably attached to the blade holder, wherein the tabs 30 are essentially planar, i.e., flat, and lie in a plane defined by the cutting blade 20 and extending beyond the cutting blade 20, as shown in FIGS. 3 and 4. Typically, the cutting blade 20 is preferably set within the cutting head 10 at an angle of about 25° from the bottom 36 of cutting head 10. In any case, the cutting blade 20 is preferably attached to the blade holder 22 at an angle of less than 90° with respect to top surface 24 of the blade holder 22. In this manner, tab 30 is attached to the blade holder 22 such that the tab 30 extends beyond the cutting blade 20 and is angled relative to the top surface 24 at essentially the same angle as the cutting blade. By use of two (2) tabs 30 as shown in FIGS. 3 and 4, one of the tabs 30 can replace the use of a prior art insertion tool or forceps for handling the blade assembly 18. In this embodiment, one of the tabs 30 is simply grasped by the fingers of a user and the other tab 30 is used to align the blade assembly 18 in order for the blade assembly to be slid into cutting head 10 without damage to cutting blade 20.

In another embodiment (not shown), it is possible that only one tab 30 could be used for replacement of an insertion tool. In this case, tab 30 would not need to lie within the same plane as cutting blade 20 but could be attached to blade holder 22 in another configuration, such as parallel to top surface 24.

FIG. 3 shows a top view of an embodiment in accordance with the present invention having two (2) tabs 30 attached to blade holder 22 which is attached to blade 20. Obviously, the attachment of blade holder 22 to blade 20 can be accomplished in several known ways. For instance, blade holder 22 may be cold or heat staked to cutting blade 20 through apertures in blade 20. In addition, blade holder 22 can be attached to cutting blade 20 via adhesive or through the use of mating male and female indentations in cutting blade 20 and blade holder 22. In any case, fingers 32 are sufficiently thin to easily detach from blade holder 22 as shown in FIG. 4, but yet are rigid enough to support tabs 30 in the desired location when one tab is being held by a user in order to assist with the insertion of the blade assembly 18 into slot 12 without damage to cutting blade 20.

We claim:

1. A blade assembly for use in a microkeratome during eye surgery, the blade assembly comprising:

a cutting blade;

a blade holder attached to the blade; and at least one tab attached to the blade holder, wherein the tab is essentially planar and lies inn a plane defined by the cutting blade and extending beyond the cutting blade, and wherein the tab is detachable from the blade holder by a twisting motion.

2. A blade assembly for use in a microkeratome during eye surgery, the blade assembly comprising:

a cutting blade;

a blade holder attached to the blade; and a pair of opposing planar tabs attached to the blade holder, wherein each of the tabs lies in a plane defined by the cutting blade and extending beyond the cutting blade, and wherein each of the tab is detachable from the blade holder a twisting motion.

* * * * *